United States Patent [19]

Stare

[11] Patent Number: 4,487,679
[45] Date of Patent: Dec. 11, 1984

[54] POTASSIUM ION-SELECTIVE ELECTRODE

[75] Inventor: Daniel R. Stare, Pittsford, N.Y.

[73] Assignee: Eastman Kodak Company, Rochester, N.Y.

[21] Appl. No.: 589,963

[22] Filed: Mar. 15, 1984

[51] Int. Cl.$^3$ ............................................. G01N 27/30
[52] U.S. Cl. .................................... 204/418; 204/416; 204/435
[58] Field of Search ............... 204/416, 418, 1 A, 435, 204/420

[56] References Cited

U.S. PATENT DOCUMENTS

| | | | |
|---|---|---|---|
| 4,053,381 | 10/1977 | Hamblen et al. | 204/416 |
| 4,171,246 | 10/1979 | Hamblen et al. | 204/1 T |
| 4,214,968 | 7/1980 | Battaglia et al. | 204/418 |
| 4,272,328 | 6/1981 | Lynch et al. | 204/1 T |

Primary Examiner—G. L. Kaplan
Attorney, Agent, or Firm—Arthur H. Rosenstein

[57] ABSTRACT

An improved potassium ion-selective electrode comprises a support having thereon a metal layer, a metal halide layer, an electrolyte layer and a potassium ion-selective membrane layer. The electrolyte layer comprises a mixture of salts, sodium halide and potassium halide at a weight ratio of sodium halide to potassium halide of 1:1 to 19:1, resulting in maintained precision and accuracy of results and improved adhesion between the electrolyte layer and adjacent layers. Preferably, the ratio of sodium halide to potassium halide in the electrolyte layer is approximately 3:1.

6 Claims, No Drawings

POTASSIUM ION-SELECTIVE ELECTRODE

FIELD OF THE INVENTION

This invention relates to dry-operative ion-selective electrodes comprising a metal layer, a layer of metal salt, an electrolyte layer and a membrane layer for the assay of potassium ions in fluids.

BACKGROUND OF THE INVENTION

In the diagnosis and treatment of various diseases as well as in preventative health checkups, it is becoming increasingly important to monitor the concentrations of certain ions (e.g. cations) in a patient's body. One cation which has merited considerable attention is potassium. High serum potassium levels are known to cause changes in muscle irritability, respiration and myocardial functions. Low potassium levels can cause excitatory changes in muscle irritability and myocardial function. Therefore, serum potassium determination has become an important diagnostic tool in the diagnosis and treatment of illness.

A useful tool in assaying for potassium has been the ion-selective electrode. One type of ion-selective electrode useful in determining ion concentration in body fluids has an electrode body (usually a glass or plastic container) containing a reference solution in contact with a half-cell of known potential (a reference electrode) and an ion-selective membrane located in an aperture in the electrode body. The ion-selective membrane is mounted in such a fashion that, when the electrode is immersed in the unknown solution, the membrane contacts both the reference and unknown solutions. A metal probe coated with a layer of insoluble salt of the metal in the reference solution and immersed therein serves as one of the contacts for measuring the potential between the electrodes and provides a reference potential for the electrode. The sensitivity of the electrode to an ion in solution is determined by the composition of the membrane. This type of electrode is referred to in the art as a "barrel" electrode.

A significant advance in the ion-selective electrode art is the dry-operative electrode described in U.S. Pat. No. 4,214,968 (issued July 29, 1980 to Battaglia et al). Prior to the discovery of such dry-operative ion-selective electrodes, electrodes had to be either stored in an aqueous solution or treated with aqueous solution just prior to use in an ion-activity-determining operation. The term "dry-operative" refers to an ion-selective electrode which provides reproducible potentiometric determination of ion activity, which is related to the ion concentration of an aqueous test solution, with no requirements for wet storage or preconditioning prior to use.

One of the specific ion-selective electrodes disclosed in the examples of Battaglia et al is a potassium ion-selective electrode. This ion-selective electrode comprises a hydrophobic ion-selective membrane coated over a reference electrode. The reference electrode consists of an electrolyte layer and a metal/metal salt reference electrode. The metal/metal salt reference electrode comprises a conductive layer of a metal in conducting contact with a layer of salt of a metal and a dry electrolyte layer in contact with the metal salt layer.

The second member of the metal/metal salt reference electrode comprises the electrolyte layer. Preferably, the electrolyte layer is a dried hydrophilic layer. The dried electrolyte solution of the ion-selective electrode comprises a hydrophilic binder having a salt in solid solution therewith. Preferably, the anion of the salt is common to the salt of the metal salt layer and the cation of said salt comprises the ion which the electrode is designed to detect. Hence, potassium chloride is the salt described and used solely in the examples of the Battaglia et al patent (as well as other disclosures pertaining to potassium ion-selective electrodes).

It has long been accepted that for optimum performance in detecting potassium ions with a potassium ion-selective electrode which uses silver chloride as the insoluble metal salt, potassium chloride is the best choice as the electrolyte since it is known that the electrode responds best to potassium ions. Therefore, although mixtures with other salts may be used, potassium chloride is a logical choice in a potassium selective electrode which uses silver chloride as the insoluble metal salt.

A substantial amount of salt other than the potassium salt would not be expected to provide equivalent precision and accuracy due to decreased available potassium ions at the reference layer/membrane layer interface.

However, a problem encountered with the use of this prior art electrode is that the adhesion between the ion-selective membrane and the metal salt layer is poor. This causes some electrodes to delaminate. Electrodes in this condition cannot be sold. This leads to wasted materials because these ion-selective electrodes must be discarded.

There is, therefore, a need for a dry-operative potassium ion-selective electrode which maintains excellent precision and accuracy and provides good adhesion between the coated layers.

SUMMARY OF THE INVENTION

In accordance with this invention, a dry-operative potassium ion-selective electrode is constructed with an electrolyte layer comprising a mixture of sodium halide and potassium halide. The substitution of the sodium ion for the commonly accepted potassium ion in the electrolyte layer does not adversely affect the precision or accuracy of the electrode and the use of the mixture of sodium halide and potassium halide in a ratio of greater than 1:1 and equal to or less than 19:1 in the electrolyte layer enhances the adhesion between that layer and the adjacent layers of the electrode.

DETAILED DESCRIPTION OF THE INVENTION

The dry-operative potassium ion-selective electrode comprises: (a) a metal/metal salt reference electrode; (b) the electrolyte layer; and (c) a potassium ion-selective membrane. The electrodes are made by a process and using components which are described in U.S. Pat. No. 4,214,968 (noted hereinabove), the disclosure of which is hereby incorporated by reference. As used throughout this specification and in the claims, the expressions, "dry-operative", "dried" and "uniform" have the meanings defined in that patent. The use of the hydrophilic binder in the electrolyte layer is optional, but preferred.

The electrodes of this invention can be used to determine the concentration of potassium in an aqueous solution, e.g. biological fluid such as whole blood, intracellular fluids, blood sera and urine. Generally, a portion of the solution to be assayed is brought into contact with the dry-operative ion-selective electrode described hereinabove which is capable of generating a potential related to the potassium ion concentration. Subsequently, the difference in potential between the portion of aqueous solution and the reference electrode is measured. Preferably, a drop of the aqueous solution is spotted onto the potassium ion-selective membrane of such electrode with a pipette or other suitable means, but other ways of contacting the electrode with the solution are acceptable.

The conductive metal layer comprises any suitable conductive metal of the well-known types which have been used in such electrodes. Particularly useful conductive metal layers include suitably thin layers of silver, nickel and platinum.

The salt layer in contact with the conductive layer comprises substantially any insoluble salt of the metal of the conductive layer which establishes a fixed interfacial potential with the metal of the conductive layer. Such layers are well known. These layers generally comprise a salt of the metal which is a product of the oxidation of the metal, as, for example, AgCl, $Hg_2Cl_2$, etc. A highly preferred embodiment utilizes the aforementioned well-known $Ag/Ag_nX$ (where $X = S^-$, $Cl^-$, $Br^-$ or $I^-$ and $n = 1$ or 2) interface to establish the potential of the reference electrode.

The potassium ion-selective electrode of the present invention contains an electrolyte layer comprising sodium halide and potassium halide, preferably NaCl and KCl. The preferred weight ratio of NaX:KX required to generate discernable interlayer adhesion improvement while maintaining the precision and accuracy of the electrode is from approximately 1:1 to approximately 19:1 and most preferably is approximately 3:1.

The membrane layer generally includes an inert hydrophobic binder or matrix having dispersed therein an ion carrier (ionophore) which imparts selectivity to the membrane. The carrier is dissolved in a carrier solvent to provide adequate potassium ion mobility in the membrane. The carrier solvent can also serve as a plasticizer for the membrane layer. Valinomycin is the preferred ion carrier. Other specific ion carriers, solvents and the like are described in U.S. Pat. No. 4,214,968. The preferred carrier solvents are aromatic and aliphatic ethers, phosphonates and phosphates and mixtures thereof, phthalates and sebacates. The assay is carried out using the potentiometric method described in U.S. Pat. No. 4,214,968.

The following examples are presented to illustrate the practice of this invention:

The dry-operative electrodes used in these examples were of the format and prepared by the methods described by the Battaglia et al patent referenced hereinabove. In general, each electrode comprised a polyester support having layers in sequence as follows: silver/silver chloride reference electrode; electrolyte layer; and the membrane layer.

EXAMPLE 1

An improved potassium ion-selective electrode was prepared as described in Battaglia et al according to the format shown below. Several additional control potassium ion-selective electrodes were prepared according to the same format except that they contained 100% KCl as the electrolyte salt as opposed to the improved electrode which contained 75% NaCl and 25% KCl.

| | PREFERRED EMBODIMENTS | |
|---|---|---|
| | | Ranges (g/m$^2$) |
| Membrane Layer | Poly(vinyl chloride-co-vinyl acetate) (90:10 weight ratio) | 2–12 |
| | Diisodecylphthalate | 2–24 |
| | Valinomycin | 0.1–2.0 |
| | DC-510 ® Surfactant | .01–.15 |
| Electrolyte Layer | Gelatin | 2–10 |
| | NaCl-KCl (3:1 mole ratio) | 1–5 |
| | Surfactant 10G ® | .01–.05 |
| | Glycerol | 0.1–0.5 |
| Reference | AgCl | 1–3 |
| | Ag | 3–6 |
| Support | poly(ethylene terephthalate) | |

The electrodes were each subjected to the tape-peel adhesive test. The tape-peel adhesive test is a standard test used to determine the force necessary to peel the membrane layer from the electrolyte layer to which it is coated. The test encompasses preparing 12.7 cm to 15.25 cm pieces of the ion selective electrodes, cutting the samples in half, scoring the edge of the samples with a knife, taking a 20 cm strip of tape, folding over on one end (1 centimeter) and placing the unfolded edge of the tape on the edge of the coated strips with the tape parallel to the coated strip and pressing with a rubber roller. A one centimeter strip is then cut from one side of the sample lengthwise, a hole is punched in the one centimeter sample to attach a hook onto an instrument to measure the weight necessary to separate the portions of the sample. The amount of force necessary to separate the layers per square centimeter is then recorded by conventional means. The more force necessary to separate the layers, the stronger the adhesion is deemed to be. The data shown in Table I clearly demonstrate the great improvement in adhesion using the modified formula of the present invention.

TABLE I

| | Electrode (% KCl:NaCl) | Tape-Peel Adhesion g/16 mm strip |
|---|---|---|
| (1) | 100:0 | 25.1 |
| (2) | 75:25 (average of 5 electrodes) | approx. 70 |
| (3) | 50:50 (average of 5 electrodes) | approx. 150 |
| (4) | 25:75 (average of 5 electrodes) | 321.1 |

EXAMPLE 2

The electrodes prepared as in Example 1 were tested for precision by determining the Coefficient Of Variation. Coefficient Of Variation is defined as $S \div \overline{X} \times 100\%$, to determine the standard deviation "S" about a mean $\overline{X}$ using a number of replicates. A lower number indicates better precision. Results of duplicate tests are shown in Table II.

TABLE II

| | Electrode (% KCl:NaCl) | % COV |
|---|---|---|
| (1) | 100:0 | 1.0 |
| (2) | 25:75 | 0.66 |
| (3) | 100:0 | 1.03 |
| (4) | 25:75 | 1.12 |

Thus, the precision at a 25:75 KCl:NaCl ratio is equivalent to that of a 100% KCl-containing electrolyte.

EXAMPLE 3

The two electrodes described in Examples 1-2 were each tested with various test fluids to determine the effects, if any, of matrix variation on the results. The test fluids comprised of samples derived from pooled human serum from Eastman Kodak Company's internal testing operations[1] and several commercial fluids obtained from Dade Corporation[2], Ortho Diagnostics[3] and Hyland Laboratories[4].

The predicted concentrations obtained from each electrode using the different control fluids are shown in Table III. There is excellent correlation between the state-of-the-art electrode and the modified formulation.

TABLE III

| | | Predicted Concentration (mEq/L) | |
|---|---|---|---|
| | Test Fluid | SOA | Example |
| (1) | [1]MP-3343-1 | 5.76 | 5.72 |
| (2) | [1]MP-4062-1 | 1.94 | 1.94 |
| (3) | [2]Monitrol 1 | 5.98 | 5.93 |
| (4) | [3]Ortho (Abnormal) | 6.56 | 6.52 |
| (5) | [4]Hyland-I | 3.29 | 3.29 |
| (6) | [4]Hyland-II | 6.39 | 6.37 |
| (7) | [1]MP123-1 | 9.59 | 9.57 |

EXAMPLE 4

Upon evaluation of the performance of ion-selective electrodes for the determination of K+ relative to the adhesion of adjacent layers, it was determined that at a ratio greater than 95:1 NaCl:KCl acceptable precision and accuracy are not obtained.

Several electrodes were prepared having varying NaCl:KCl weight ratios, shown in Table IV. Each element was tested in duplicate using a variety of test fluids (described above). The Coefficients Of Variation were determined for each. Results, shown in Table IV, indicate that electrodes having up to 95% or less NaCl are within the acceptable COV limit whereas the electrode with more than 95% NaCl is not.

TABLE IV

| | Precision Results Using Various Weight Ratios of NaCl:KCl | | |
|---|---|---|---|
| Electrode | % NaCl:KCl | Test 1 | Test 2 |
| Control 1 | 100:0 | 1.15 | 0.72 |
| 1 | 75:25 | 0.88 | 0.90 |
| 2 | 75:25 | 0.66 | 1.03 |
| 3 | 85:15 | 0.82 | 1.07 |
| 4 | 95:5 | 1.10 | 1.76 |
| Control 2 | 99:1 | 1.57 | 2.26 |
| Acceptable pooled % COV | | <1.20 | <1.80 |

EXAMPLE 5

The data set generated for Example 4 was used to determine the accuracy of the described electrodes. A mean (average predicted concentration) was established using the electrodes of Table IV. Acceptably accurate results are within two standard deviations (SD) from the mean ($\overline{X}$). Results shown in Table V indicate that assays obtained using Control 2 (1% KCl) are unacceptable whereas those using the preferred embodiment of the present invention (25% KCl) are acceptable.

TABLE V

| | | | Assays | |
|---|---|---|---|---|
| Test Fluid | $\overline{X}$ | 2 S.D. range | 1% KCl | 25% KCl |
| Ortho I | 6.50 ± .04 | 6.46-6.54 | 6.34 | 6.47 |
| Hyland I | 3.37 ± .05 | 3.32-3.42 | 3.30 | 3.37 |
| Kodak | 4.40 ± .05 | 4.35-4.45 | 4.30 | 4.38 |
| Ortho II | 6.38 ± .08 | 6.30-6.46 | 6.16 | 6.39 |
| Hyland II | 6.37 ± .09 | 6.28-6.46 | 6.12 | 6.39 |

Thus, it is seen that at greater than 19:1 sodium chloride to KCl ratio the accuracy of the test electrode does not fall within the acceptance standard for accuracy.

While the invention has been described in detail with particular reference to preferred embodiments, thereof, it will be understood that variations and modifications can be effected within the spirit and scope of the invention.

What is claimed is:

1. In a dry-operative potassium ion-selective electrode comprising:
   (a) a dried internal reference electrode comprising a metal/metal salt reference electrode, said reference electrode comprising a conductive layer of a metal in contact with a layer of an insoluble salt of a metal, and a dried electrolyte layer comprising the dried residue of a water soluble salt having, as an anion, the anion of said metal salt layer and a hydrophilic polymeric binder in a solvent for the polymer and salt; and
   (b) in contact with the reference electrode a hydrophobic ion-selective membrane of predetermined uniform thickness in regions intended for contact with a sample for analysis, said membrane comprising an ion carrier dissolved in a carrier solvent; the improvement comprising a mixture of sodium halide and potassium halide in a weight ratio from 1:1 to 19:1 in said electrolyte layer.

2. The electrode of claim 1, wherein the ratio of sodium halide to potassium halide in said electrolyte layer is 3:1.

3. The electrode of claim 1, wherein the halide in said electrolyte layer is chloride.

4. The electrode of claim 1, wherein the ion carrier is valinomycin.

5. The electrode of claim 1, wherein the carrier solvent is selected from the group consisting of aromatic and aliphatic ethers, phosphonates and phosphates and mixtures thereof, phthalates and sebacates.

6. The electrode of claim 1 wherein the carrier solvent is diisodecylphthalate.

* * * * *